United States Patent [19]

Komatsu

[11] 4,170,994
[45] Oct. 16, 1979

[54] PLASTIC CONTAINERS FOR PARENTERAL SOLUTIONS

[75] Inventor: Kyoichi Komatsu, Naruto, Japan

[73] Assignee: Otsuka Pharmaceutical Factory, Inc., Japan

[21] Appl. No.: 806,064

[22] Filed: Jun. 13, 1977

Related U.S. Application Data

[62] Division of Ser. No. 616,266, Sep. 24, 1975, abandoned.

[51] Int. Cl.² ............................................. A61M 5/16
[52] U.S. Cl. ........................... 128/214 C; 128/214 D; 128/272; 215/32; 222/541
[58] Field of Search ........... 128/214 R, 214 C, 214 D, 128/214.2, 227, 272, DIG. 24, 216; 215/32; 222/107, 215, 541

[56] References Cited

U.S. PATENT DOCUMENTS

| 2,571,059 | 10/1951 | Puschelberg | 128/214 C |
| 2,687,727 | 8/1954 | Lawshe | 128/216 |
| 3,081,002 | 3/1963 | Tauschinski et al. | 128/DIG. 24 |
| 3,171,412 | 3/1965 | Braun | 128/272 |
| 3,419,172 | 12/1968 | Lee | 222/541 X |
| 3,951,148 | 4/1976 | Herb | 128/214 D |

FOREIGN PATENT DOCUMENTS

| 1337891 | 8/1963 | France | 128/214 R |
| 2006024 | 12/1969 | France | 128/214 D |
| 360763 | 4/1962 | Switzerland | 128/272 |

*Primary Examiner*—Dalton L. Truluck
*Attorney, Agent, or Firm*—McGlew and Tuttle

[57] ABSTRACT

A plastic container for a parenteral solution comprising a main body and a tubular portion extending downward from the lower end of the body and having a closed end openable by cutting, the tubular portion being formed in its outer peripheral surface with a groovelike recess for indicating the cutting position and reducing the wall thickness of the tubular portion at the cutting position; and a combination of the above plastic container and an administration device having one end to be liquid-tightly connected to the tubular portion of the container when it is opened and the other end having an injection needle.

5 Claims, 10 Drawing Figures

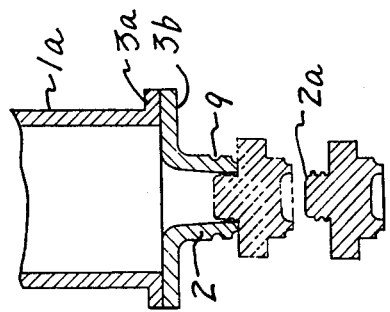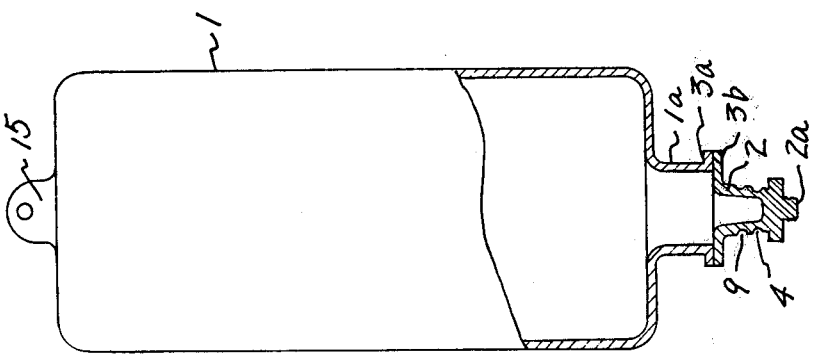

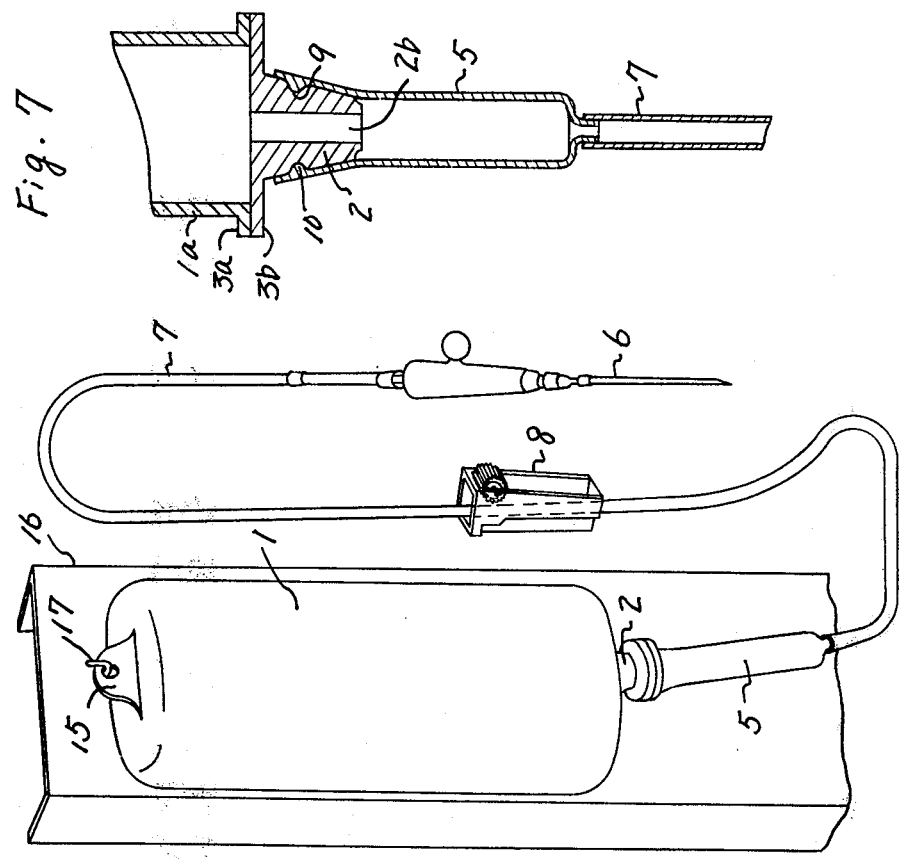

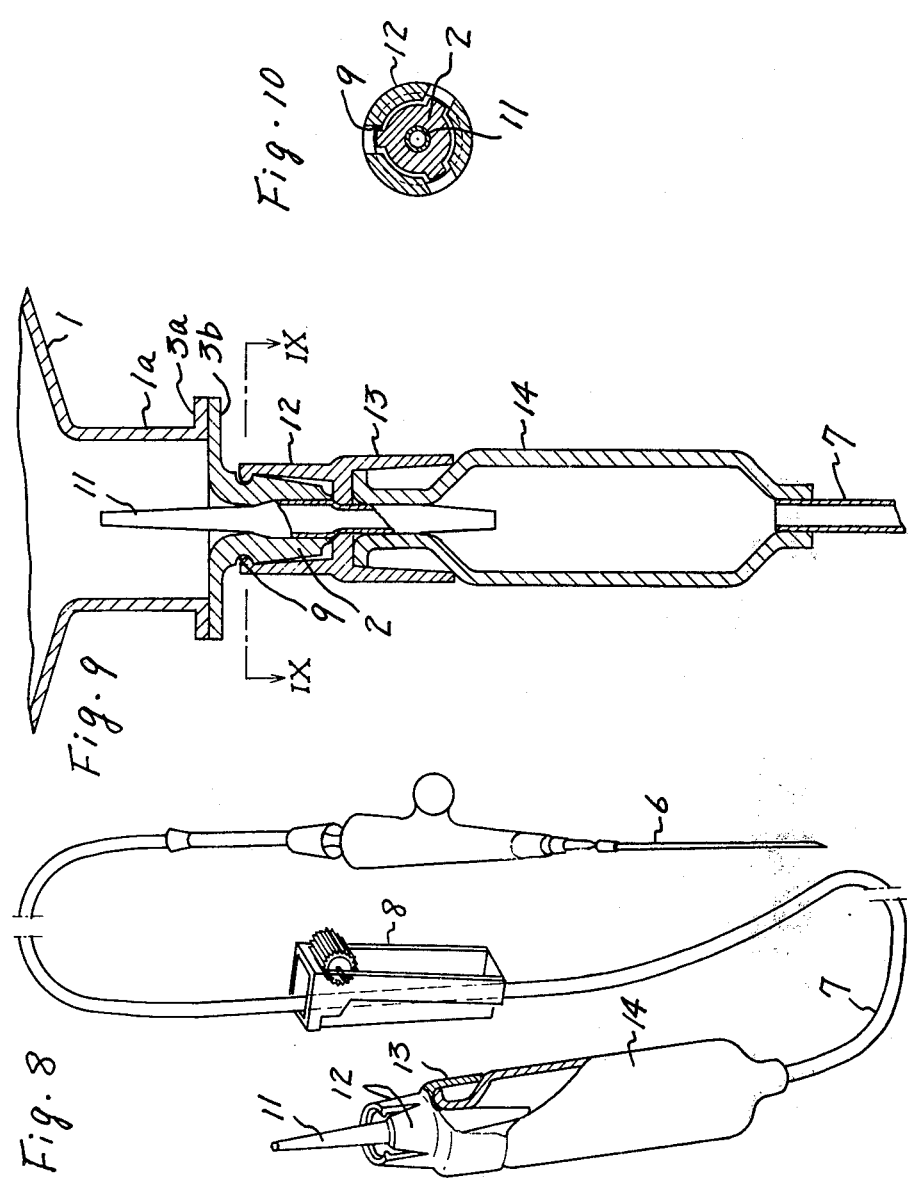

PLASTIC CONTAINERS FOR PARENTERAL SOLUTIONS

This is a division of application Ser. No. 616,266 filed Sept. 24, 1975, now abandoned.

FIELD OF THE INVENTION

This invention relates to plastic containers for parenteral solutions such as physiologic saline solution, Ringer's solution and like electrolytic solutions and carbohydrate solution, amino acid solution and like nutritional solutions.

DESCRIPTION OF THE PRIOR ART

Among the above-mentioned solutions to be administered to the patient, relatively inexpensive solutions such as physiologic saline solution and Ringer's solution are also used to wash the affected part during operation. Accordingly containers for these solutions must be adapted for the withdrawal of the enclosed solution with use of an administration device and, moreover, it is desired that they are easily openable at the outlet portion thereof. The solution administration device generally comprises a hollow needle to be passed through the closure of the container, a tube for conducting the solution from the needle to an injection needle and a clamp mounted on the tube for regulating the flow rate of the solutions.

Although glass bottles with a rubber stopper have been used as containers for the aforesaid solutions, they are heavy and fragile. In recent years, therefore, there has been a tendency to use plastic containers in place of glass bottles.

Heretofore known as plastic container for parenteral solutions are:
(a) Those having a closure made of the same material as the container and heat-sealed to the outlet thereof,
(b) Those with a rubber stopper closing the outlet of the container, and
(c) Those including a rubber stopper closing the outlet of the container and a plastic diaphragm disposed within the neck of the container inwardly of the stopper.

With plastic containers of type (a), however, the outlet is not readily openable and no consideration is given to the solution for use as a washing solution for the affected part.

In the case of plastic containers of type (b), the rubber stopper directly contacts the solution, possibly causing contamination of the solution due to the reaction between the rubber and solution.

Plastic containers of type (c), which include both the plastic diaphragm and the rubber stopper, are complicated in construction and are not easy to manufacture. In addition, the outlet is not readily openable and the containers therefore have the same drawbacks as type (a).

With the foregoing constructions (a), (b) and (c), furthermore, the closing member must be pierced by the hollow needle of the administration device for the withdrawal of solution, so that the hollow needle must at least be formed with a sharp metal tip. However, a fragment of rubber or plastic is then likely to clog up the opening at the extremity of the tip when the needle pierces the rubber or plastic closing member. Thus the liquid passage needs to be opened at the side of the needle tip. For these reasons, the hollow needle becomes very complex in construction and expensive.

SUMMARY OF THE INVENTION

An object of this invention is to provide a plastic container for a parenteral solution having an outlet which is easy to open when so desired to assure extreme convenience when the solution is used to wash the affected part of the patient.

Another object of this invention is to provide a plastic container for parenteral solution which has no rubber stopper to assure safety of the solution from contamination by any reaction product of the rubber and solution.

Another object of this invention is to provide a plastic container for parenteral solution which is simple in construction and easy to manufacture.

Still another object of this invention is to provide a plastic container for parenteral solution from which the solution can be withdrawn by a device of simple construction to eliminate the necessity to use an expensive hollow needle.

The above and other objects of this invention will become apparent from the following description.

This invention provides a plastic container for parenteral solution comprising a main body and a tubular portion extending downward from the lower end of the main body and having a closed end openable by cutting, the tubular portion being formed in its outer peripheral surface with a groovelike recess for indicating the cutting position and reducing the wall thickness of the tubular portion at the cutting position.

The plastic container of this invention can be opened by cutting the tubular portion at the position of the groovelike recess. The solution within the container is administered to the patient by an administration device having a portion to be liquid-tightly connected to the opened end of the tubular portion. Furthermore by causing the solution to flow out directly from the opened end of the tubular portion, the solution is applicable to the affected part for washing.

The plastic container of this invention is usable both for administering the solution to the patient and for washing the affected part with the solution. Because the container is wholly made of plastics, it is free of contamination of the solution which would be experienced with the use of rubber stopper and is extremely simple in construction and easy to manufacture.

Since the present plastic container itself is readily openable and the administration device to be used in combination therewith is easily connectable to the opening of the container to withdraw the solution, the device need not be equipped with an expensive hollow needle conventionally required to pierce the closure.

According to the invention, the container is produced from plastics by a known method for example by blow molding. As plastics, it is preferable to use polyethylene, polypropylene and like having high transparency and good flexibility. The container may have at the midportion of its upper end a tab for suspending the container from a support. The wall thickness of the main body of the container, which is not particularly limited, is preferably such that the container is deformable as the internal pressure decreases with the withdrawal of the solution. To ensure this, the wall thickness is preferably about 0.3 to 1.0 mm when the container is made of polyethylene or polypropylene.

The tubular portion at the lower end of the body is molded integrally with or separately from the body.

When separately molded, the tubular portion is joined to the open end of the body by high frequency or ultrasonic heating after the solution has been placed into the body.

The tubular portion has an outer diameter of 5.0 to 25.0 mm, preferably of 7.0 to 15.0 mm, and an inner diameter of 3.0 to 15.0 mm, preferably 4.0 to 8.0 mm. The inner diameter and the outer diameter are suitably selectively determined within the above-mentioned ranges so that the difference therebetween, namely the wall thickness of the tubular portion, will be 2.0 to 10.0 mm, preferably 3.0 to 7.0 mm. To facilitate the connection of the tubular portion to the administration device, the tubular portion can be gently tapered.

The tubular portion is formed in its outer peripheral surface with a groovelike recess to indicate the position where the tubular portion is cut, to reduce its wall thickness at the cutting position and to facilitate the engagement of scissors or like cutter means for the purpose of cutting. The groovelike recess may be formed over the entire periphery of the tubular portion, or at least two recesses may be provided partially of the periphery for example at two opposing positions. Above the groovelike recess, the tubular portion can be provided with an engaging portion for connection to the administration device. When the part of the tubular portion below the groovelike recess, namely the end part thereof to be cut off to open the container, is so shaped as to snugly fit in the opening of the tubular portion formed by cutting, the cut-off part is usable as a plug for the opened tubular portion.

BRIEF DESCRIPTION OF THE DRAWINGS

This invention will be described below with reference to the accompanying drawings showing embodiments of the invention.

FIG. 3 is a view partly in vertical section showing another embodiment of this invention in which the part to be cut off from a tubular portion is usable as a plug;

FIG. 4 is a view in vertical section of the principal part of the embodiment of FIG. 3 in which the plug is shown as fitted in the opened tubular portion;

FIG. 5 is a perspective view showing an embodiment of administration device to be used for the container of this invention;

FIG. 6 is a perspective view showing the embodiment of FIG. 5 as it is being used for withdrawing an solution from the container illustrated in FIG. 2;

FIG. 7 is a view in vertical section showing the embodiment of FIG. 6 as connected to the tubular portion of the container;

FIG. 8 is a perspective view showing another embodiment of administration device to be used for the container of this invention;

FIG. 9 is a perspective view showing the embodiment of FIG. 8 as it is being used for withdrawing a solution from the container of FIG. 2; and FIG. 10 is a view in cross section taken along the line IX—IX in FIG. 9 and showing an exemplary mode of engagement of gripping pieces in a groove.

DESCRIPTION OF THE PREFERRED EMBODIMENTS

Figure 2:
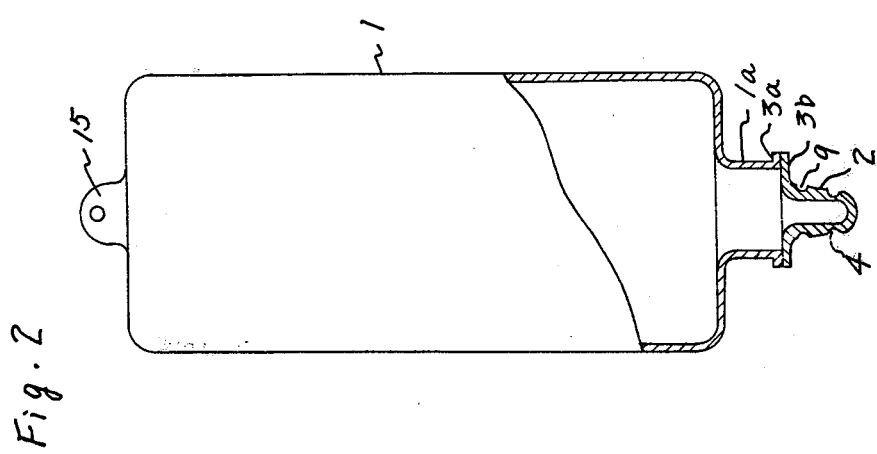
FIG. 2 is a view partly in vertical section showing another embodiment of this invention including a main body and a tubular portion each molded separately.
Figure 1:
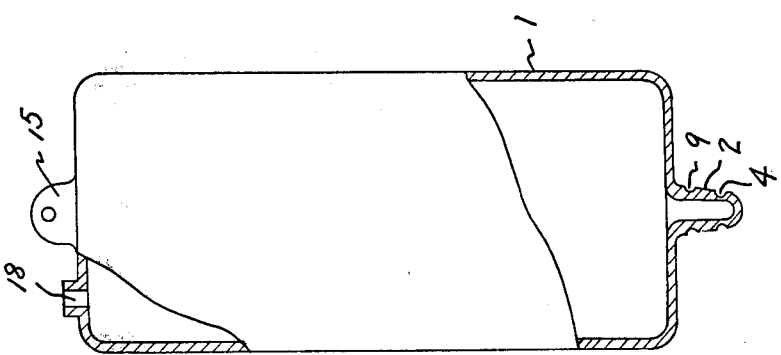
FIG. 1 is a view partly in vertical section showing an embodiment of this invention including a main body and a tubular portion integrally molded therewith.

Basically the plastic container of this invention comprises a main body 1 and a tubular portion 2 which are molded integrally (see FIG. 1) or separately (see FIGS. 2 and 3).

When the body 1 and tubular portion 2 are integrally molded, a solution is placed into the body 1 through an inlet 18 at the upper end of the body 1. After the solution has been placed, the inlet 18 is heat-sealed.

When the body 1 and the tubular portion 2 are separately molded, the solution is placed into the body 1 through the open end of neck 1a of the body 1. In this case, the inlet 18 need not be provided. After the solution has been placed, the tubular portion 2 is joined to the open end of the neck 1a in known manner as by high frequency heating or ultrasonic heating. For this purpose, it is preferably to form flanges 3a and 3b at the ends of the neck 1a and of the tubular portion 2 and to join the flanges 3a and 3b together face-to-face by heating as seen in FIGS. 2 and 3.

The tubular portion 2 is formed with a groovelike recess 4 in its outer peripheral surface. To open the container, the tubular portion 2 is cut at the position of the groovelike recess 4. Since the grooved part 4 has a smaller thickness than the other portion and is readily engageable with cutter means such as scissors, the tubular portion 2 is easy to cut at this part.

When the portion 2a to be cut off from the tubular portion 2 has an end so shaped as to be snugly fittable in the opening of the tubular portion 2 formed by cutting, the portion 2a is usable as a plug.

In the case where the solution is used to wash the affected part, the solution is run off from the end of the tubular portion 2 opened by cutting. Washing can be done easily as desired by manually pressing and deforming the body 1 to force out the solution.

The patient is given the solution from the container suspended from a support 16 by the engagement of hook 17 of the support 16 in a tab 15 on the upper end of the container and with use of an administration device as shown in FIGS. 5 and 8.

The administration device shown in FIG. 5 has a cylindrical connector 5 to be connected to the tubular portion 2 of the container. The cylindrical connector 5 is connected to an injection needle 6 by a outlet tube 7 equipped with a clamp 8 to regulate the flow of the solution. The cylindrical connector 5, made of soft synthetic resin such as polyethylene, is tightly fitted over the tubular portion 2 due to its elasticity. (see FIGS. 6 and 7). The cylindrical connector 5 has an inner diameter corresponding to the outer diameter of the tubular portion 2 and is therefore fittable around the tubular portion 2. The tubular portion 2 has a tapered outer peripheral surface which ensures easy and tight engagement with the cylindrical connector 5. The base end of the tubular portion 2 is formed in its outer peripheral surface with a groove 9 in which an inner peripheral projection 10 at one end of the cylindrical connector 5 is engageable, whereby the cylindrical connector 5 can be prevented from disengagement from the tubular portion 2.

The solution within the body 1 flows through a passage 2b in the tubular portion 2 into the cylindrical connector 5 and is administered to the patient by way of the outlet tube 7 and needle 6. The solution flows down dropwise into the cylindrical connector 5 when flowing out from the open end of the passage 2b (see FIG. 7), so that the cylindrical connector 5, when transparent, is serviceable also as a drip chamber. Alternatively, the drip chamber may be provided independently of the cylindrical connector 5.

The administration device shown in FIG. 8 includes a cannula 11 to be intimately inserted into the tubular portion 2 for connection to the container. Generally the cannula 11 can be made of hard synthetic resin such as acrylonitrile-butadiene-styrene copolymer resin and rigid polyvinyl chloride resin. Integral with the cannula 11 are gripping pieces 12 engageable in the groove 9 of the tubular portion 2. The illustrated embodiment has three gripping pieces 12 which are equidistantly spaced apart and arranged concentrically with the cannula 11. When the cannula 11 is inserted into the tubular portion 2, the gripping pieces 12 engage in the groove 9 of the tubular portion 2 to prevent the removal of the cannular 11 (see FIG. 9). Only two gripping pieces 12 may be provided as opposed to each other, or at least four gripping pieces 12 may be formed as spaced apart equidistantly. When the groove 9 is formed discontinuously in corresponding relation to the gripping pieces 12, the cannula 11 can be held to the tubular portion 2 against rotation (see FIG. 10).

A cylindrical portion 13 concentric with the cannula 11 can be provided to the rear of the gripping pieces 12. The cylindrical portion 13 is grasped when the administration device is to be connected to the container, while when pressed on to disengage the gripping pieces 12 from the groove 9, the cylindrical portion tends to open the gripping pieces to facilitate the disengagement. The rear end of the cannula 11 is connected to the outlet tube 7 by a drip chamber 14.

What is claimed is:

1. An administration device comprising, a plastic parenteral solution container (1) including a tubular container body having parenteral solution therein and being sealed around its periphery and having a small tubular extension (2) projecting outwardly from the bottom end thereof, said tubular extension (2) having a closed outer end and having at least two substantially parallel spaced encircling grooves (9,4) arranged in spaced relationship to the outer end thereof, one of said grooves closest said outer end defining a reduced wall thickness (4) for easy severance across said groove (4) to form a tubular portion (2) with an open passage (2b) therethrough for opening the tubular extension for removal of the solution from the container (1), another of said grooves (9) defining a dispensing device engagement recess, and an administration device (5) having one top elastically expandable end to be liquid-tightly connected to said open tubular portion (2) of the container (1), the other end of said device (5) having an injection needle connection (7) connected thereto, said elastically expandable end of said device (5) having an interior annular bead (10) engaged to said one of said grooves (9) for holding said device (5) to said tubular portion (2), said device (5) having a chamber between said tubular portion (2) and said injection needle connection (7) defining a drip chamber.

2. An administration device according to claim 1 wherein said tubular extension (2) includes a flange portion (3b) adjacent said container (1), and said container (1) includes a neck portion (1a) terminating in a flange (3a) adjacent said flange (3b) of said tubular extension (2), said two flanges (3a, 3b) being heat-fused to each other, said container (1) and tubular extension (2) being made of plastic.

3. An administration device according to claim 1, wherein said outer end of said tubular extension (2) comprises a plug portion (2a), said plug portion (2a) having a reduced diameter plug end of a diameter substantially equal to that of said open passage (2b), whereby after the easy severance across said groove (4) said plug end is adapted for use in closing off said open passage (2b).

4. An administration device comprising, a plastic parenteral solution container (1) including a tubular container body having parenteral solution therein and being sealed around its periphery and having a small tubular extension (2) projecting outwardly from the bottom end thereof, said tubular extension (2) having a closed outer end and having at least two substantially parallel spaced encircling grooves (9,4) arranged in spaced relationship to the outer end thereof, one of said grooves closest said outer end defining a reduced wall thickness (4) for easy severance across said groove (4) to form a tubular portion (2) with an open passage (2d) therethrough for opening the tubular extension for removal of the solution from the container (1), another of said grooves (9) defining a dispensing device engagement recess, and an administration device (5) having one top elastically expandable end to be liquid-tightly connected to said open tubular portion (2) of the container (1), the other end of said device (5) having an injection needle connection (7) connected thereto, said elastically expandable end of said device (5) having an interior annular bead (10) engaged to said other one of said grooves (9) for holding said device (5) to said tubular portion (2), said device (5) having a chamber between said tubular portion (2) and said injection needle connection (7) defining a drip chamber, said top elastically expandable end comprising a plurality of circumferentially spaced gripping pieces (12) each having a portion of said interior annular bead (10), said other of said grooves (9) being discontinuous and extending only in the area of said bead portions on said plurality of gripping pieces (12), whereby said device (5) is prevented from rotating with respect to said container (1) when said device (5) is liquid-tightly connected to said open tubular portion (2), said device (5) further including a cylindrical portion (13) extending substantially axially from said gripping pieces (12) in a direction away from said container (1) said drip chamber comprising a separate member (14) having a top portion connected into said cylindrical portion (13) in the vicinity of said gripping pieces (12), whereby said cylindrical portion (13) is grasped and squeezed radially inwardly to move said gripping pieces (12) radially outwardly and facilitate engagement and disengagement of said device (5) with said tubular portion (2).

5. An administration device according to claim 4 further including a cannular (11) axially aligned with said gripping pieces (12) and cylindrical portion (13) and connected thereto by an intermediate wall connecting said gripping pieces (12) to said cylindrical portion (13), said cannular extending into said open passage (2b) and into said drip chamber element (14).

* * * * *